United States Patent
Phillips

[11] Patent Number: 6,165,227
[45] Date of Patent: *Dec. 26, 2000

[54] ATTACHMENT CONSTRUCTION FOR PROSTHESIS

[76] Inventor: Van L. Phillips, P.O. Box 1873, Rancho Santa Fe, Calif. 92067

[*] Notice: This patent is subject to a terminal disclaimer.

[21] Appl. No.: 08/643,829

[22] Filed: May 7, 1996

Related U.S. Application Data

[63] Continuation of application No. 08/208,793, Mar. 8, 1994, Pat. No. 5,514,186, which is a continuation of application No. 07/856,666, Mar. 24, 1992, abandoned, which is a continuation-in-part of application No. 07/337,374, Apr. 13, 1989, Pat. No. 5,181,932, and a continuation-in-part of application No. 07/662,783, Feb. 28, 1991, Pat. No. 5,290,319.

[51] Int. Cl.$^7$ ...................................................... A61F 2/66
[52] U.S. Cl. .................................................... 623/53
[58] Field of Search .......................... 623/38, 47, 52–56, 623/50, 39, 44, 46

[56] References Cited

U.S. PATENT DOCUMENTS

| | | | |
|---|---|---|---|
| 61,780 | 2/1867 | Watson . | |
| 277,562 | 5/1883 | Furrer . | |
| 1,220,648 | 3/1917 | Leader . | |
| 1,804,915 | 5/1931 | Collins . | |
| 2,379,538 | 7/1945 | Meierhofer . | |
| 2,440,075 | 4/1948 | Campbell . | |
| 2,475,372 | 7/1949 | Caltranis . | |
| 2,543,908 | 3/1951 | Guzey . | |
| 2,692,392 | 10/1954 | Benington et al. . | |
| 2,731,645 | 1/1956 | Woodall | 623/53 |
| 2,897,512 | 8/1959 | Sackett | 623/39 |
| 3,400,408 | 9/1968 | Garcia . | |
| 3,422,462 | 1/1969 | Finnieston | 623/38 |
| 3,820,169 | 6/1974 | Long . | |
| 3,889,301 | 6/1975 | Bonner, Sr. . | |
| 4,007,496 | 2/1977 | Glabiszewski . | |
| 4,007,497 | 2/1977 | Haupt | 623/50 |
| 4,089,072 | 5/1978 | Glabiszewski . | |
| 4,225,982 | 10/1980 | Cochrane et al. . | |
| 4,328,594 | 5/1982 | Campbell et al. . | |
| 4,360,931 | 11/1982 | Hampton . | |
| 4,547,913 | 10/1985 | Phillips . | |
| 4,608,054 | 8/1986 | Schroder . | |
| 4,619,661 | 10/1986 | Axelsson . | |

(List continued on next page.)

FOREIGN PATENT DOCUMENTS

| | | | |
|---|---|---|---|
| 2501999 | 3/1981 | France . | |
| 2626463A | 1/1988 | France . | |
| 2640499 | 12/1988 | France . | |
| 2410998 | 6/1998 | France . | |
| 295807 | 3/1915 | Germany . | |
| 325171 | 9/1920 | Germany . | |
| 0389252 | 2/1924 | Germany | 623/53 |
| 366553 | 1/1973 | Germany . | |
| 135800 | 5/1979 | Germany . | |
| 3214772C1 | 8/1983 | Germany . | |
| 605613 | 4/1978 | U.S.S.R. . | |
| 778732 | 12/1980 | U.S.S.R. . | |
| 1600759A | 10/1990 | U.S.S.R. . | |
| 277760 | 9/1927 | United Kingdom . | |
| 2070439 | 9/1981 | United Kingdom | 623/47 |
| 2099950 | 12/1982 | United Kingdom . | |
| 2202448A | 9/1988 | United Kingdom . | |

OTHER PUBLICATIONS

Gueyraud, *Experimentation Clinique D'Une Prosthese De Membre Inferieru Eu Materizux Composites*, Marseille, 1987.

*Primary Examiner*—David H. Willse
*Attorney, Agent, or Firm*—Knobbe, Martens, Olson & Bear, LLP

[57] ABSTRACT

A prosthetic pylon attachment construction provides a useful attachment interface between the exterior of a pylon which otherwise has a generally curvilinear exterior and a broad range of other prosthetic devices having relatively flat attachment surfaces, and permits ready manufacture and ready interchangeability of a range of prosthetic devices and pylons.

5 Claims, 12 Drawing Sheets

U.S. PATENT DOCUMENTS

| | | |
|---|---|---|
| 4,645,509 | 2/1987 | Poggi et al. . |
| 4,721,510 | 1/1988 | Cooper et al. . |
| 4,792,340 | 12/1988 | Aulie et al. . |
| 4,822,363 | 4/1989 | Phillips . |
| 4,938,776 | 7/1990 | Masinter . |
| 4,959,073 | 9/1990 | Merlette . |
| 4,994,086 | 2/1991 | Edwards . |
| 5,013,325 | 5/1991 | Rennerfelt . |
| 5,037,444 | 8/1991 | Phillips . |
| 5,066,305 | 11/1991 | Firth . |
| 5,139,524 | 8/1992 | Aulie et al. . |
| 5,156,631 | 10/1992 | Merlette . |
| 5,514,186 | 5/1996 | Phillips ................................... 623/52 |

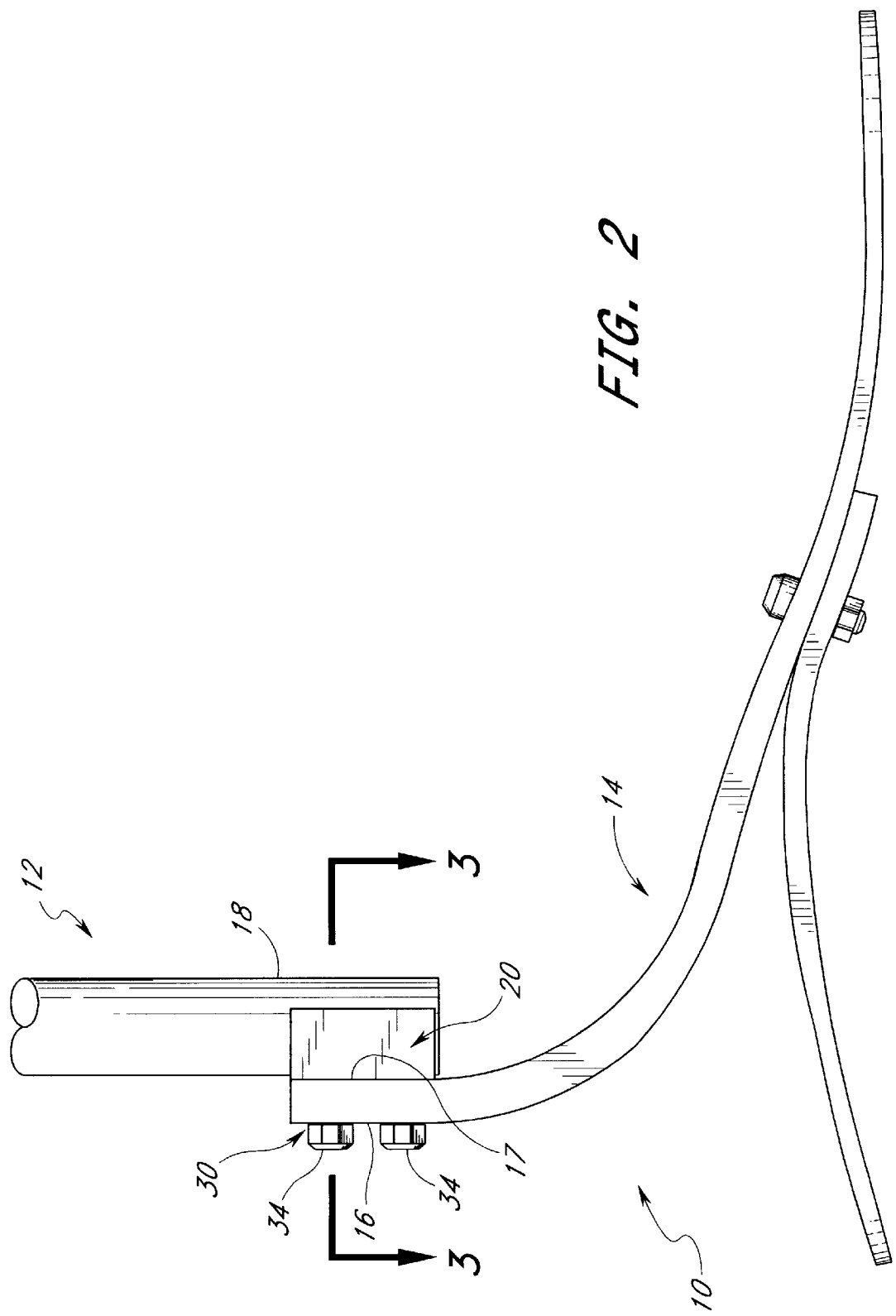

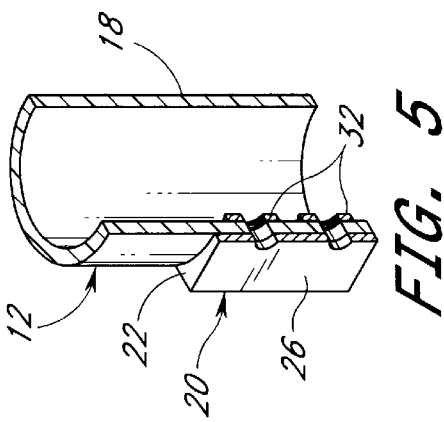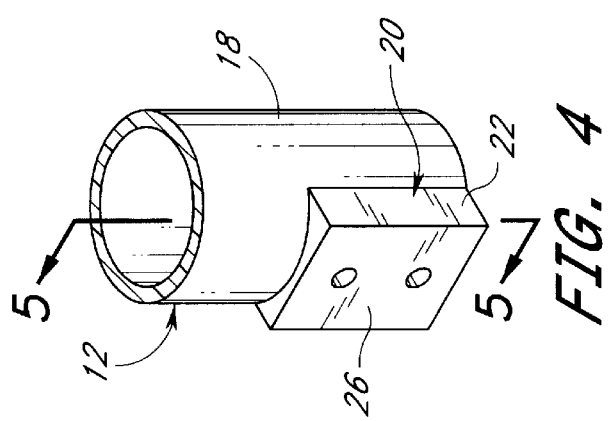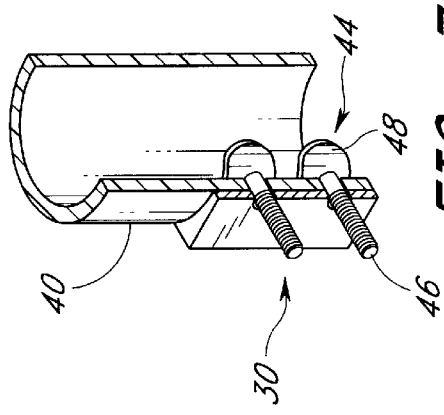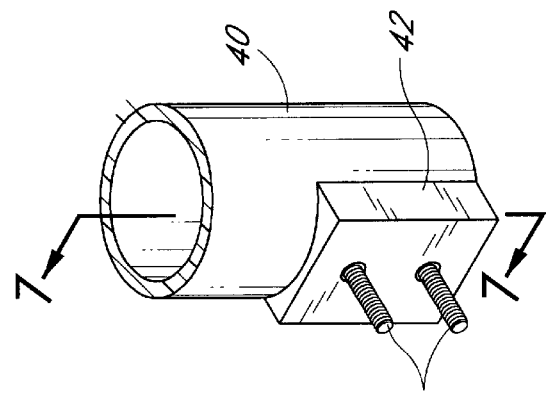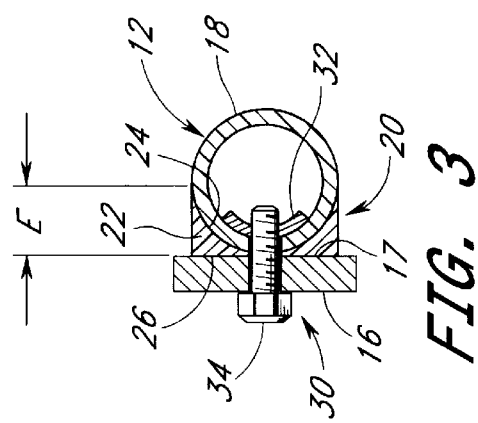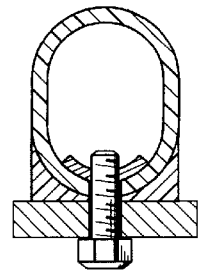

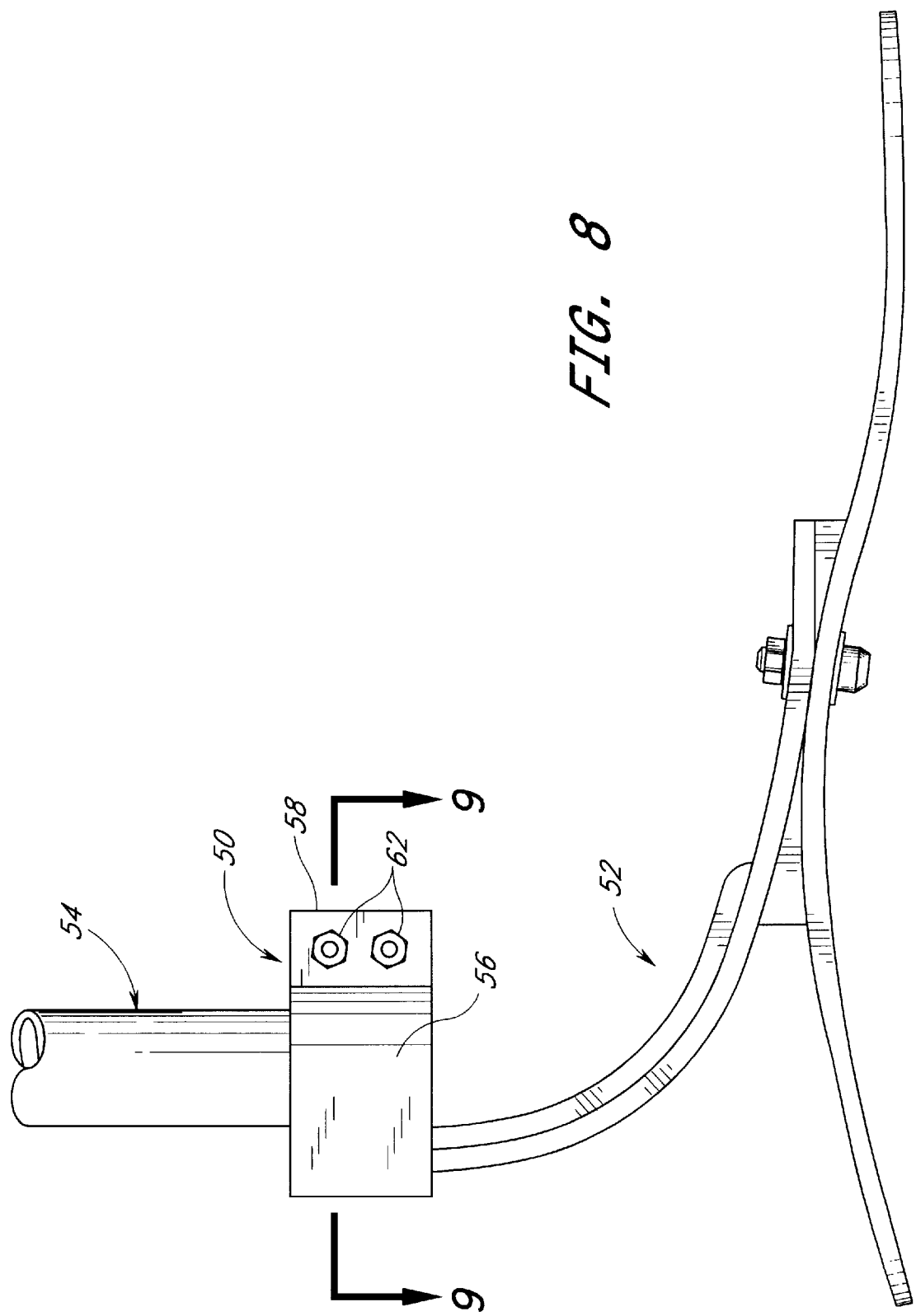

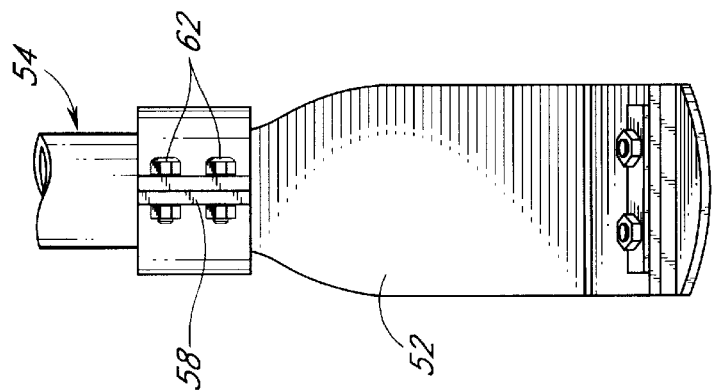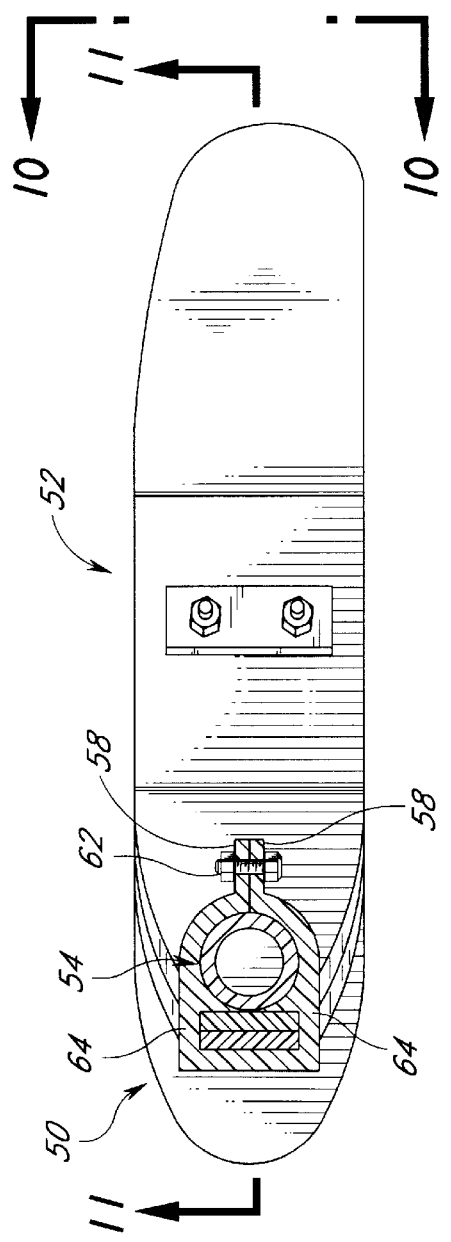

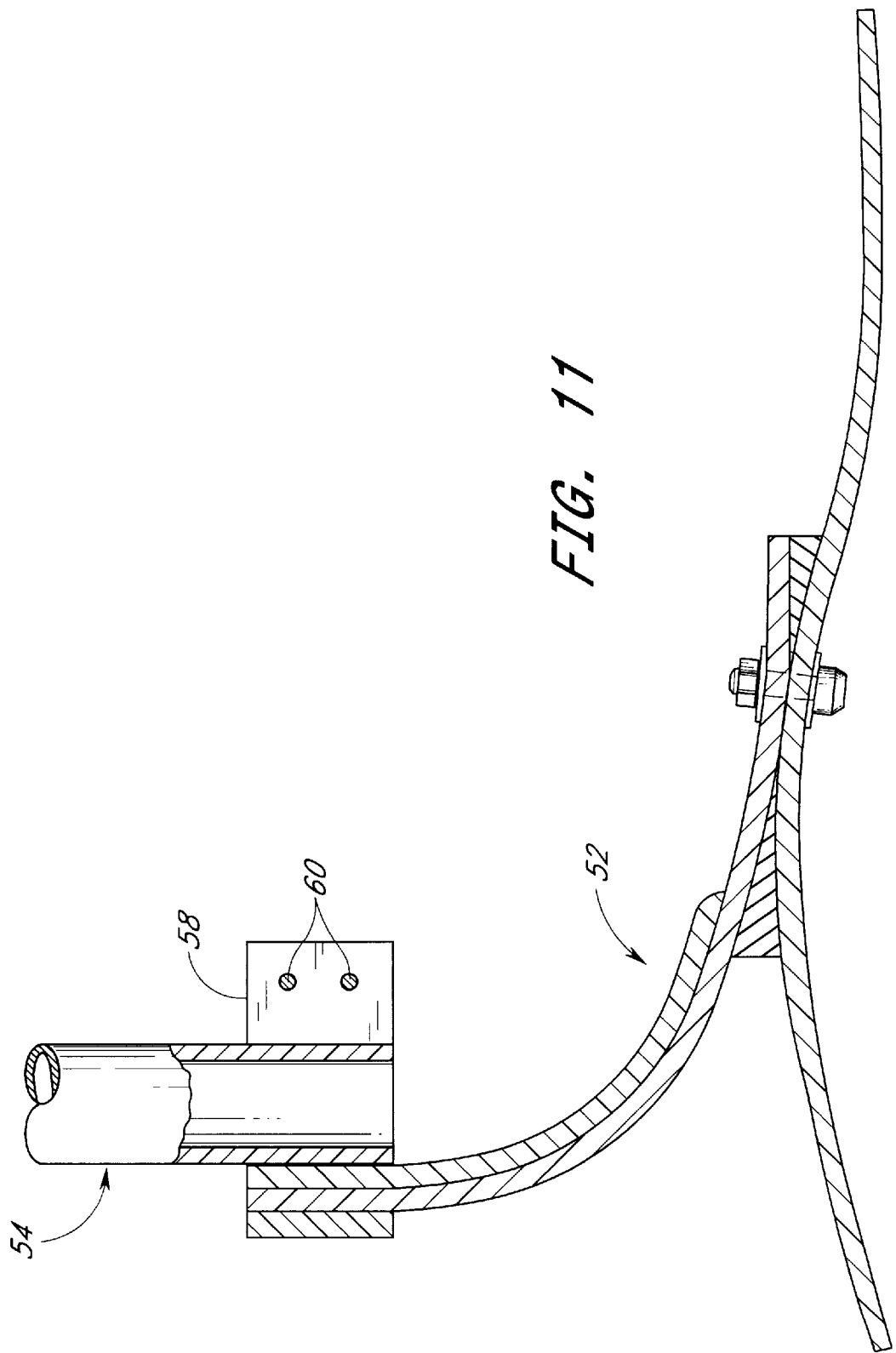

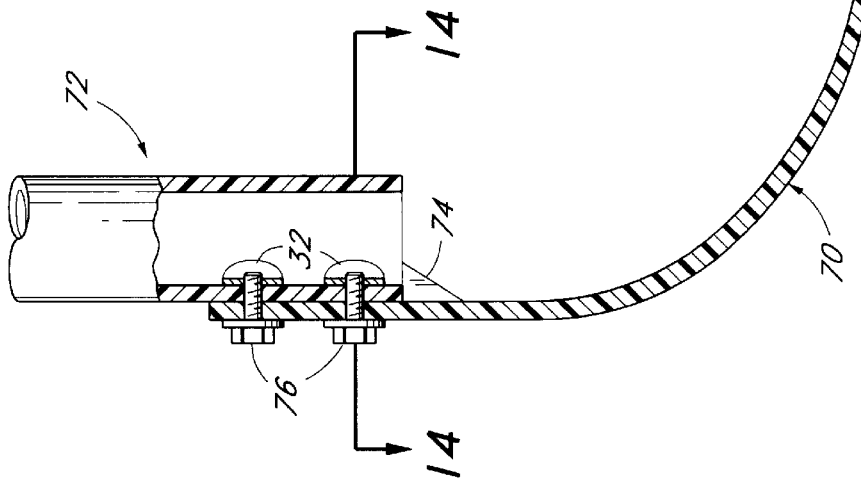
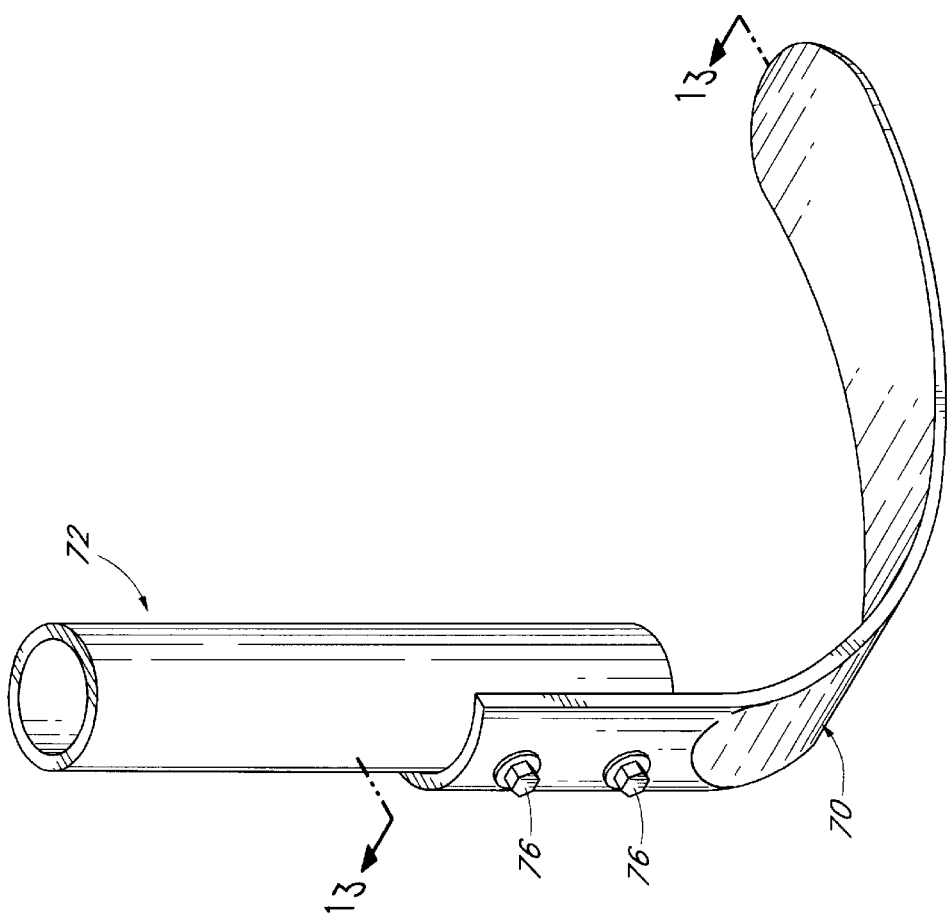

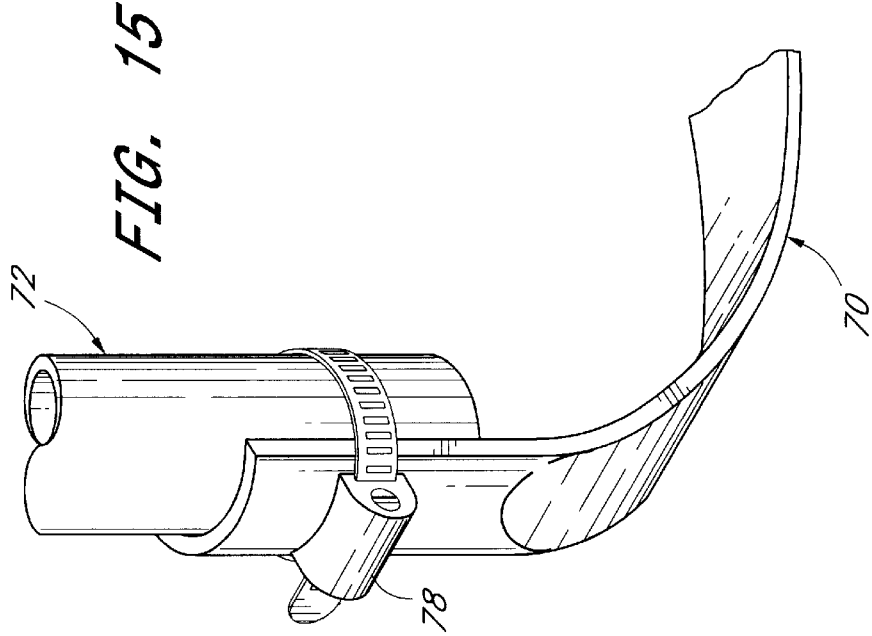
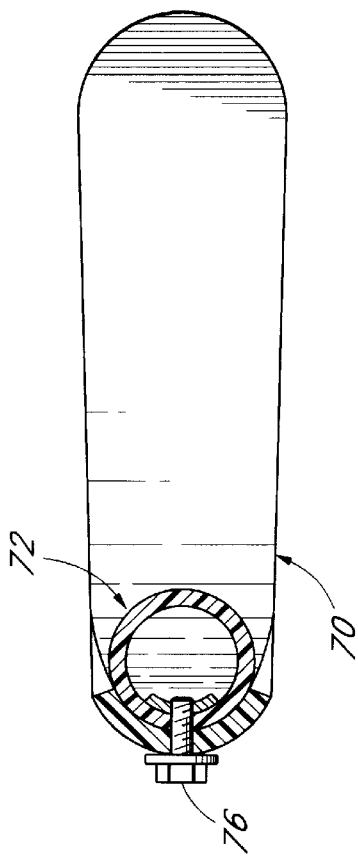
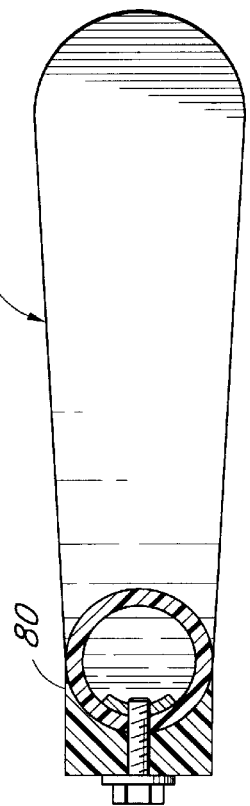

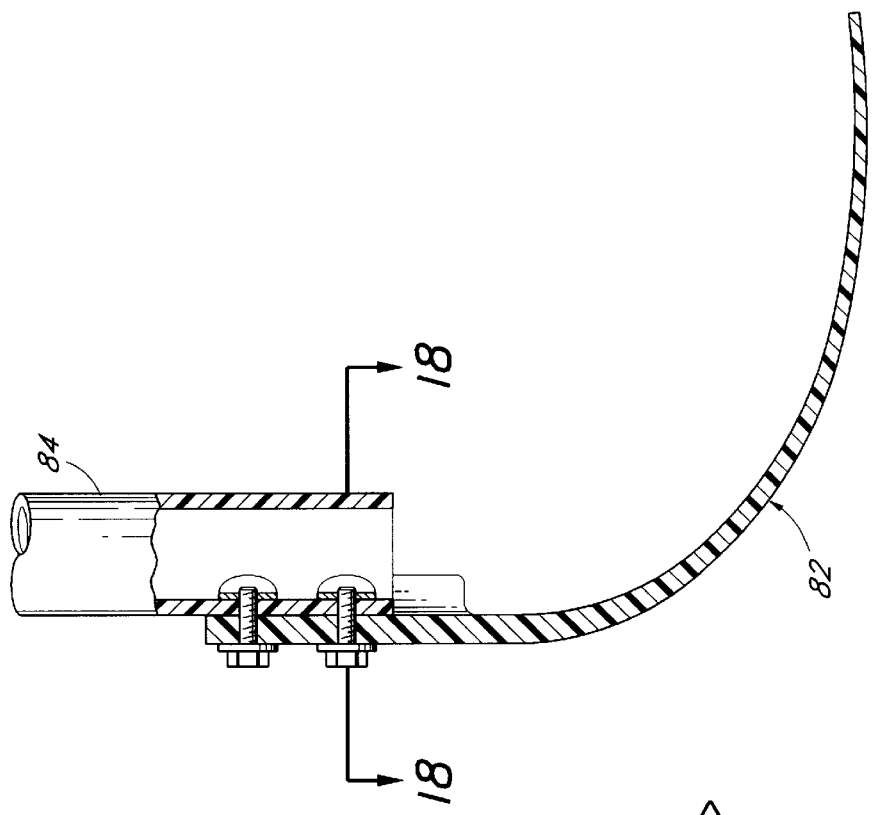
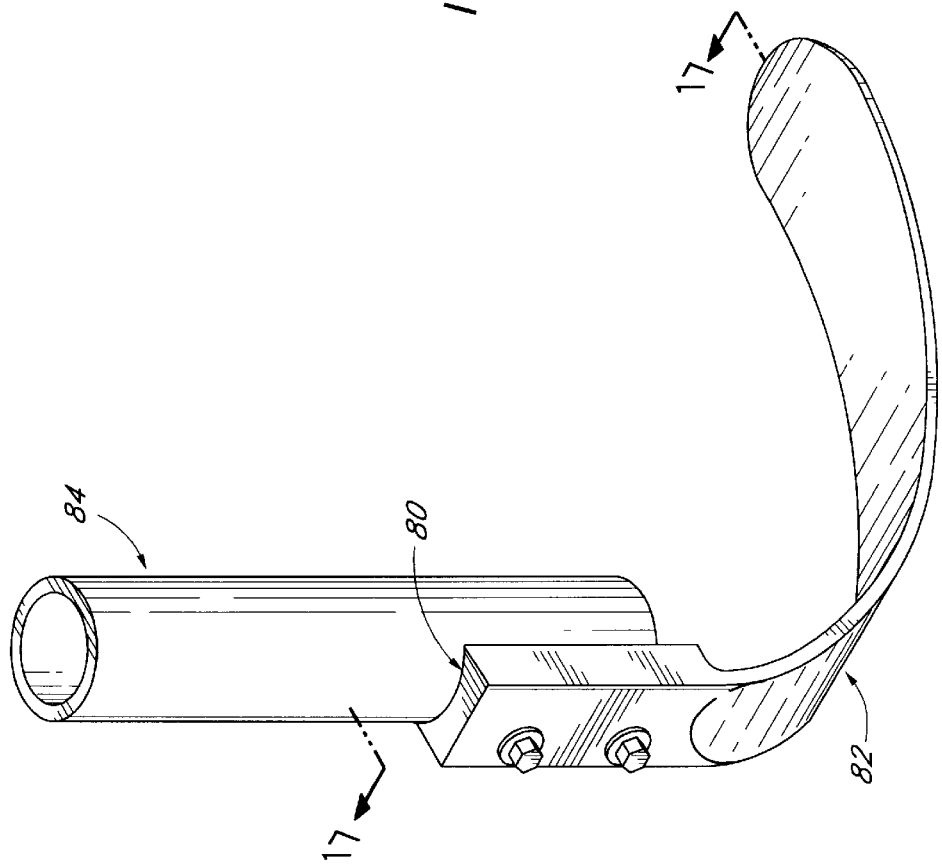

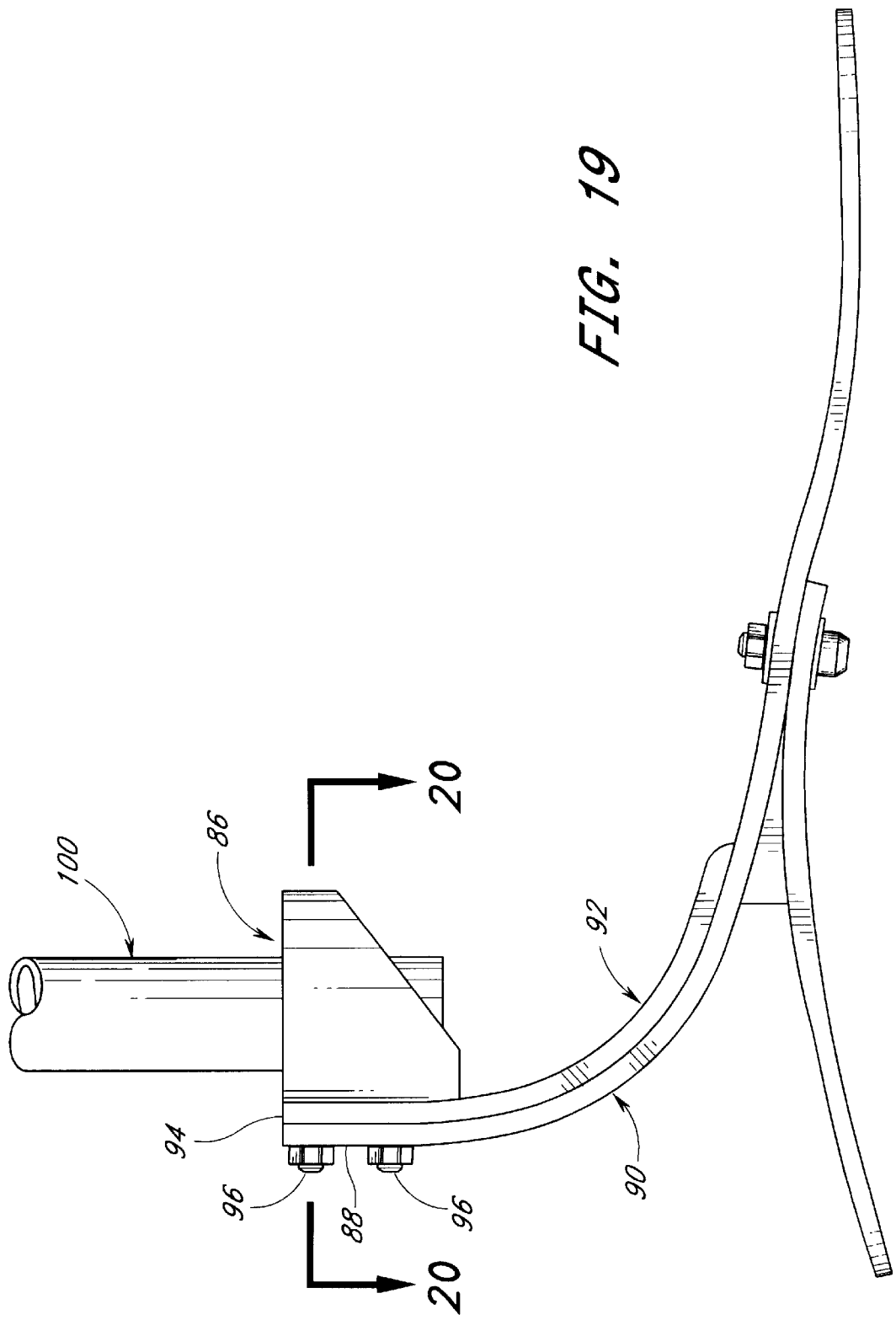

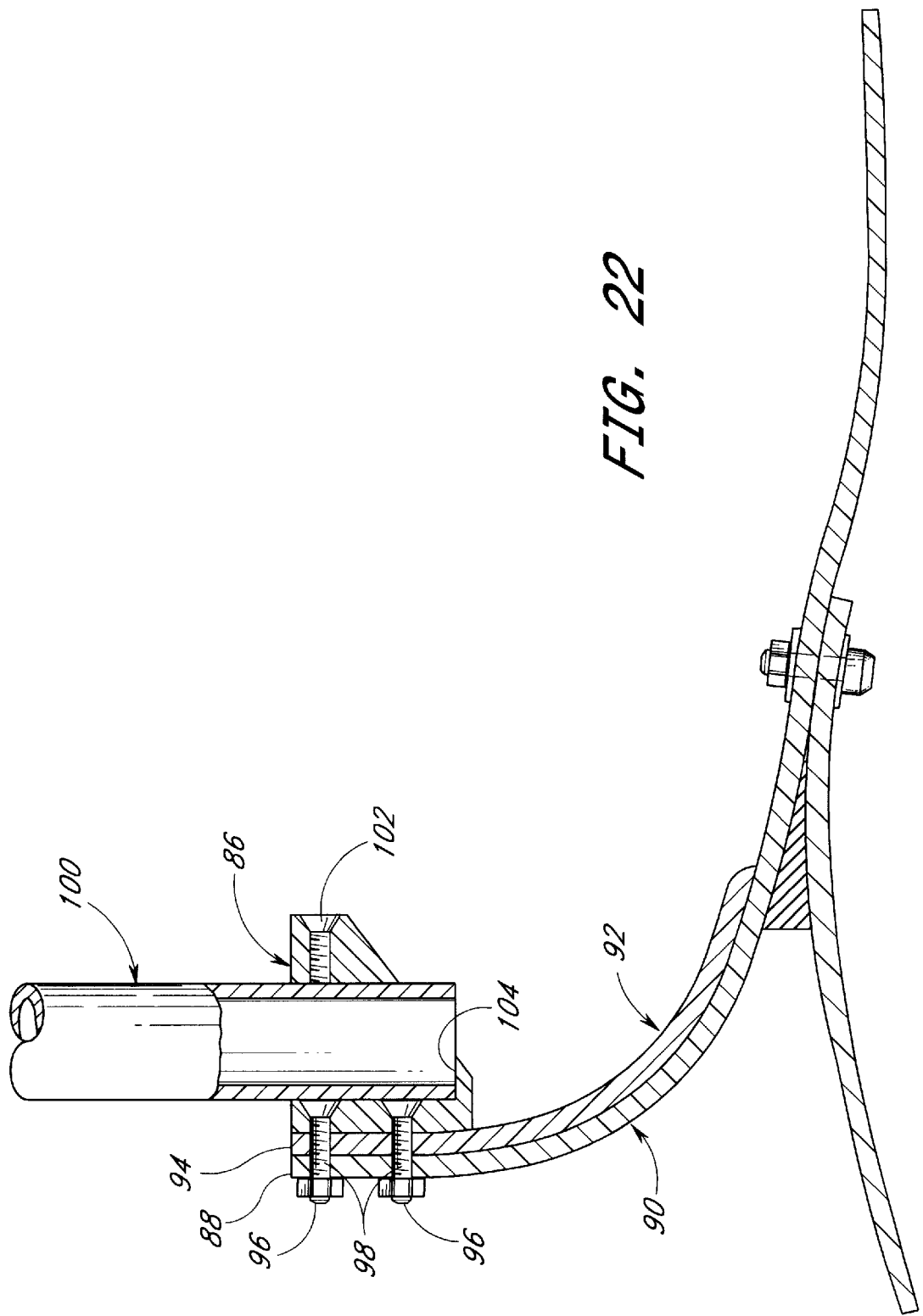

ATTACHMENT CONSTRUCTION FOR PROSTHESIS

CROSS REFERENCE TO RELATED APPLICATIONS

This Application is a continuation of Ser. No. 08/208,793, filed Mar. 8, 1994, now U.S. Pat. No. 5,514,186, which is a continuation of Ser. No. 07/856,666, filed Mar. 24, 1992, now abandoned, which is a continuation-in-part of Ser. No. 07/337,374, filed Apr. 13, 1989, now U.S. Pat. No. 5,181,932, and a continuation-in-part of Ser. No. 07/662,783, filed Feb. 28, 1991, now U.S. Pat. No. 5,290,319.

BACKGROUND OF THE INVENTION

This invention relates to prostheses in general, and specifically to a construction which permits the attachment of a prosthetic device having a relatively flat surface to the exterior of a prosthetic pylon which has a generally curvilinear exterior.

It is well known in the prosthetic arts, and particularly in the prosthetic leg art, to provide a cylindrical tubular pylon between a wearer's stump and another prosthetic device, such as a prosthetic foot. Such pylons provide a strong, lightweight extension structure between the stump and the other prostheses, which structure may typically be cut to a desirable length for a particular wearer.

Although other pylon configurations could certainly be utilized for this purpose, the cylindrical tubular pylon has numerous desirable characteristics and has therefore become the configuration of choice among many prosthetists and amputees. For example, although prosthetists could utilize solid pylons or pylons having a square or rectangular cross-section or otherwise providing a relatively flat attachment surface for other prosthetic devices, such other pylons typically are not as strong and lightweight as a cylindrical tubular pylon. Moreover, a cylindrical tubular pylon may be relatively less expensive to manufacture than pylons having more complex cross-sectional configurations or requiring more material.

Unfortunately, many of the aforesaid other prosthetic devices which would otherwise be useful in combination with the abovedescribed cylindrical tubular pylons, are not readily usable therewith because they do not have an attachment surface which conforms to the curved exterior of the pylon. Due to considerations of manufacture and/or performance, such other prosthetic devices commonly include relatively flat attachment surfaces for operable attachment to the wearer, whether or not a intermediate pylon is utilized. Thus, in order to be usable with such pylons, these other prosthetic devices must be specifically designed to include special attachment structures and/or configurations which permit attachment to the pylons.

The special designs and modifications of the prior art are not without drawbacks. For example, any such special attachment structure typically adds to the cost of manufacture of the prosthesis. In certain cases, these attachment structures are fairly bulky, weighty, and complex, because the attachment of the aforesaid other prosthetic devices to the pylon must be reliable and secure to prevent undesirable movement between the pylon and the other prosthetic device. Perhaps more importantly, the structures and configurations necessary to permit attachment to the pylons may detrimentally affect the performance of the prosthesis and/or limit the range of wearers who could otherwise benefit from its use.

Exemplary of such design accommodations is the configuration illustrated in FIG. 1 hereto, in which a foot prosthesis A is operatively attached to a tubular cylindrical pylon B through the incorporation of a curvilinear section C and the provision of an attachment mechanism D. As shown in FIG. 1, the combination of the curvilinear section C, its attachment section $C_1$, the attachment mechanism D, and its attachment section $D_1$ permits the relatively flat structure $C_1$ to be operatively retained adjacent the relatively flat bottom of the tube B. Such a structure involves a complexity and expense, and includes performance limitations, which are less than optimum.

Moreover, such a structure requires a substantial clearance beneath the pylon tube B in order to accommodate the components A, C, $C_1$, D and $D_1$ thereby limiting the range of amputees who may be served by such a construction.

OBJECT AND ADVANTAGES OF THE INVENTION

It is, therefore, an object of my invention to provide a prosthetic construction which will overcome the foregoing problems and, among other things, will permit tubular cylindrical pylons to be readily utilized with other prosthetic devices having otherwise relatively non-curved attachment surfaces. Those skilled in the art will understand, however, that various embodiments of my invention may be practiced with other types of pylons; for example, solid pylons, pylons with oval or other curved exterior cross sectional configurations, etc.

The prosthesis of my invention is characterized by a first prosthetic member (such as a pylon) having a first end attachable to a wearer and a second end including a curved external surface, a second prosthetic member having an attachment surface which is of a configuration not matingly corresponding to the curved external surface of the first prosthetic member, and a coupling construction operatively disposed between the first prosthetic member and the second prosthetic member to facilitate cooperative attachment therebetween.

As indicated above, such a construction permits the above-described popular cylindrical tubular pylon to be readily utilized with any of a broad range of other prosthetic devices having relatively flat attachment surfaces, and permits ready manufacture and ready interchangeability of a range of prosthetic devices and pylons. Economies of manufacture and standardization of parts, ease of assembly and of replacement of prosthetic components, and adjustability of the entire prosthesis are improved and enhanced.

Another object of my invention is the provision of a prosthesis of the aforementioned character which includes attachment means, such as cooperative nut, bolt, and/or clamp members, to retain the various components in the desired assembled configuration.

Yet another object of my invention is the provision of a prosthesis of the aforementioned character in which the relatively flat attachment surface or portion is provided by material affixed or bonded to the tubular pylon. A somewhat related embodiment of my invention includes a mating curvilinear surface formed by material affixed or bonded to the relatively flat attachment surface or portion or by the curvilinear formation of that attachment surface itself.

Still another object of my invention is the provision of a prosthetic pylon having a first end adapted for attachment to a wearer and a second end generally having an external surface which is curved, in which the pylon includes an attachment portion adjacent the second end of the pylon, the attachment portion providing a relatively flat or non-curved attachment surface for the attachment of prosthetic devices to the pylon.

Certainly, for prosthetic devices which include attachment sections with surfaces which are neither flat nor of correspondingly mating configuration with respect to the curved exterior of the above-described cylindrical tube, the construction of my invention may be provided in a configuration which will facilitate the desired mating between the pylon and the other prosthetic device. For purposes of standardization and interchangeability, however, it appears that the aforementioned flat surfaces are the most utilitarian.

An additional object of my invention is the provision of a leg prosthesis having a pylon with a first end attachable to a wearer and a second end including a curved external surface, and having a lower leg prosthesis including an attachment surface which is of a configuration not matingly corresponding to the curved external surface of said pylon, with an attachment construction therebetween including an attachment portion having a first surface matingly corresponding to the curved external surface of the pylon and a second surface matingly corresponding to the attachment surface of the lower leg prosthesis, and attachment means to retain the pylon, the attachment portion and the lower leg prosthesis in operative relationship with each other.

Yet another object of my invention is the provision of an improved construction for attaching a prosthetic device to a standard pylon tube. The construction of my invention permits ready attachment of a broad range of prosthetic devices to the abovedescribed cylindrical pylon, irrespective of the fact that such devices have relatively flat attachment surfaces, and permits ready manufacture and ready interchangeability of a range of prosthetic devices and pylons.

Consequently, prosthetists and wearers can select from a broad range of prosthetic devices and readily attach same to the pylon at their discretion. Through the provision of preferably demountable attachment means such as nut and bolt assemblies or gripping clamps for attaching the prosthetic device to the pylon, the pylon of my invention may be provided in standard lengths but still be readily "custom-fitted" to a wide range of effective lengths.

Other objects and advantages of the invention will be apparent from the following specification and the accompanying drawings, which are for the purpose of illustration only.

BRIEF DESCRIPTION OF THE DRAWINGS

FIG. 2 is a side elevation view of a preferred embodiment of an attachment construction in accordance with the teachings of the invention;

FIG. 3 is a sectional view, taken along line 3—3 of FIG. 2;

FIG. 3A is a sectional view of an alternative embodiment of a tubular pylon;

FIG. 4 is a perspective view of the lower end of a pylon constructed in accordance with the teachings of the invention;

FIG. 5 is a sectional perspective view, taken along line 5—5 of FIG. 4;

FIG. 6 is a perspective view of an alternative embodiment of the invention, similar to the view shown in FIG. 4;

FIG. 7 is a partially sectional, partially cutaway perspective view, taken along line 7—7 of FIG. 6;

FIG. 8 is a side elevation view of an alternative embodiment of an attachment construction in accordance with the teachings of the invention;

FIG. 9 is a partially sectional plan view, taken along line 9—9 of FIG. 8;

FIG. 10 is a front elevation view, taken along line 10—10 of FIG. 9;

FIG. 11 is a partially sectional view, taken along line 11—11 of FIG. 9;

FIG. 12 is a perspective view of an alternative embodiment of an attachment construction in accordance with the teachings of the invention;

FIG. 13 is a partially sectional view, taken along line 13—13 of FIG. 12;

FIG. 14 is a partially sectional plan view, taken along line 14—14 of FIG. 13;

FIG. 15 illustrates an alternative embodiment of attachment means for a construction otherwise similar to FIG. 12;

FIG. 16 is a perspective view of yet another alternative embodiment of an attachment construction in accordance with the teachings of the invention;

FIG. 17 is a partially sectional view, taken along line 17—17 of FIG. 16;

FIG. 18 is a partially sectional plan view, taken along line 18—18 of FIG. 17;

FIG. 19 is a side elevation view of yet another alternative embodiment of an attachment construction in accordance with the teachings of the invention;

FIG. 22 is a partially sectional view, taken along line 22—22 of FIG. 20.

DESCRIPTION OF THE PREFERRED EMBODIMENT

Figure 1:
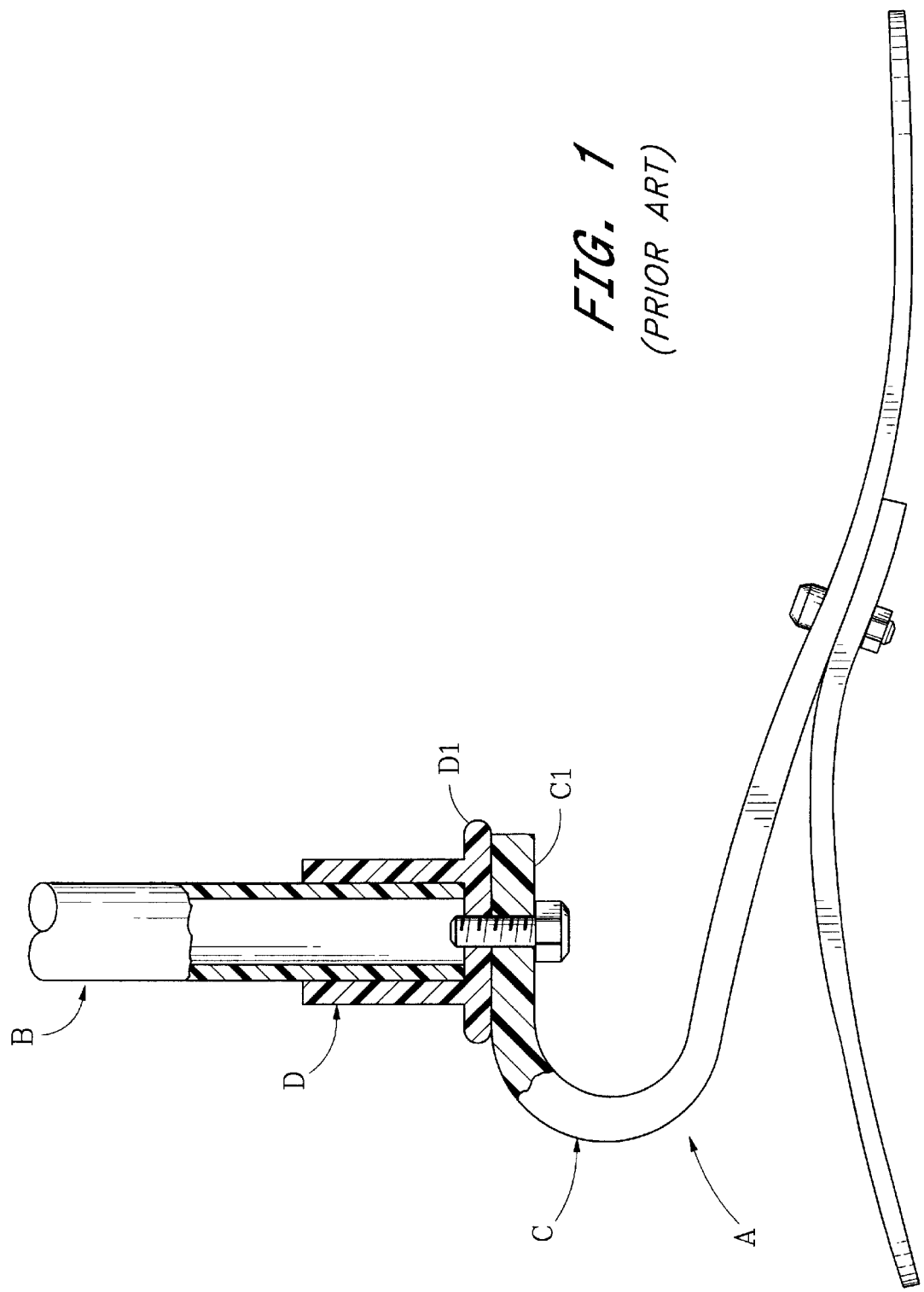
FIG. 1 is a side elevation, partly sectional view of a prosthesis illustrating a known method of attaching a prosthetic foot below a tubular cylindrical pylon.

Referring to the drawings, and particularly to FIGS. 2–5 thereof, I show a prosthesis attachment construction 10 constructed and assembled in accordance with the teachings of the invention and including a prosthetic pylon 12. As indicated above, the pylon 12 is illustrated as having a cylindrical tubular configuration; those skilled in the art will understand that other pylon configurations may benefit from the advantages of my invention such as shown in FIG. 3A, for example.

For purposes of illustration, the prosthesis 10 is shown as including a prosthetic foot 14 which incorporates an attachment section 16 having an attachment surface 17 at an upper end thereof for operatively attaching the prosthetic foot 14 to a wearer. Those skilled in the art will understand, however, that other prosthetic feet and even arm and hand prostheses may be utilized with the pylon 12 and may benefit from my invention.

In the preferred embodiment, and as will also be well understood by those skilled in the art, the pylon 12 is provided at its first or upper end (not shown) with a socket or other expedient for operative attachment to the wearer. Moreover; the pylon 12 and the foot 14 are preferably fabricated from lightweight, strong materials such as graphite, fiberglass, carbon fiber or the like, and., in the leg prosthesis illustrated in FIGS. 2–5, preferably provide desirable energy-performance characteristics to enhance the wearer's use of the prosthesis 10.

In the preferred embodiment, the pylon 12 includes a second or lower end 18 to which another prosthesis such as the prosthetic foot 14 is to be attached. In order to provide a large contact area for mating engagement between the lower end 18 and the prosthetic foot 14, a coupling or attachment construction 20 such as an attachment portion 22 is operatively disposed between the first prosthetic member 12 and the second prosthetic member 14. The relatively large contact area enhances the stability of the attachment of the foot 14 to the pylon 12, and does so in a simple and economic manner.

The attachment portion 22 may be fabricated in a wide variety of methods and materials. For example, it may be formed in a unitary construction with the pylon 12, in which case it would be of similar materials and integral therewith. Preferably, however, for reasons of ease of manufacture and considerations of economy, the attachment portion 22 is formed subsequent to the pylon 12, although it may be affixed thereto through bonding, gluing or similar expedient.

For the preferred graphite construction, the attachment portion 22 is formed of molded graphite bonded onto the exterior of the pylon 12, and may include chopped fiber or strengthening laminates. Alternative constructions would include, by way of example and not by way of limitation, casting the attachment portion 22 in a lightweight metal such as aluminum.

In the preferred embodiment, the attachment portion 22 may be conveniently described as having a first surface 24, FIG. 3, matingly corresponding to the curved external surface of the second end 18 of the pylon 12. Obviously, for embodiments in which the attachment portion 22 is formed integrally with the pylon 12, there will be no true "first surface" as just described, in the sense that the materials of the pylon 12 and the attachment portion 22 will blend into one another.

Also in the preferred embodiment, the attachment portion 22 provides a second surface 26, FIGS. 3–5, which matingly corresponds to the attachment surface 17 of the lower leg prosthesis 14, providing the above-described desirable stable contact area between the foot 14 and the pylon 12.

Weight, cost and performance considerations indicate that the attachment construction 22 preferably extend only a minimum distance from the pylon 12 in the direction E, FIG. 3. Alternative embodiments (not shown) would include provision of the attachment portion 22 of a thickness E that would space the second prosthetic member 14 relatively further from the pylon 12, but such spacing could require additional materials and would additionally offset the second prosthetic member 14 from the longitudinal axis of the pylon 12, with potentially undesirable performance effects.

In addition, the preferred embodiment of my invention includes attachment means 30 such as nut and bolt combinations 32 and 34. The attachment means 30 preferably retains the pylon 12, the attachment portion 22 and the lower leg prosthesis 14 in operative relationship with each other. Those skilled in the art will understand that any of a wide range of attachment means 30 may be utilized for this purpose. Examples of alternative attachment means include hose clamps or other frictionally-gripping clamps, such as those shown in the alternative embodiments herein, which would function by encircling the pylon end 18, the attachment portion 22, and the upper end of the foot 14.

The preferred nuts 32 are preferably threaded washers (sometimes called barrel nuts) which are curved, as best illustrated in FIG. 3, to permit their ready juxtaposition to the interior of the tubular pylon 12. In order to provide ease of assembly, the barrel nuts 32 are preferably affixed or bonded to the interior of the pylon 12. For durability and resistance to rust or other deterioration, the nuts 32 are preferably fabricated from stainless steel, titanium, or similar material.

The preferred embodiment of my invention, FIG. 3, is assembled by inserting bolts 34 through openings in the second prosthetic member 14 and the pylon 12 and into threaded engagement with the barrel nuts 32.

One of the many alternative attachment means 30 is illustrated in FIGS. 6–7. The construction is similar to that shown in FIGS. 2–5, with a pylon 40 having an attachment portion 42 disposed thereagainst.

In FIGS. 6–7, however, the attachment means 30 includes outwardly-protruding bolt means 44. Bolt means 44 may be fabricated by bonding or otherwise attaching curved washers 48 (similar to the aforedescribed barrel nuts 32) to threaded rods 46. Alternatively, bolt means 44 may be assembled by bonding barrel nuts 48 to the interior of the pylon 40 and threadedly engaging the threaded rods 46 therewith, resulting in the configuration illustrated in FIGS. 6–7.

To assemble this alternative embodiment of the prosthesis 10, the foot 14 (not shown) would be positioned so that the bolts 46 extend therethrough. Nuts (not shown) would be threadedly engaged on the ends of the bolt means 44 opposite to the barrel nuts 48 to retain the components in assembled configuration.

Another alternative embodiment would obviate the need for the barrel nuts 32. One such embodiment would involve providing threaded holes in the pylon 12, and the bolts 34 threadedly engaging only those holes instead of the barrel nuts 32.

Additionally, among the alternative embodiments of pylon tubes 12 is that the lower end 18 can be open (as shown in FIGS. 2–5) or closed (not shown) on the bottom. If barrel nuts 32 are to be installed inside the pylon 12 to provide the aforesaid attachment means, such installation would occur prior to closure of the bottom of the tube.

As will be readily understood by those skilled in the art, the attachment construction 22 may be located on any side of the pylon 12, including the back of the pylon as illustrated in FIG. 2, or the front or the sides (not shown). In any of these orientations, the attachment construction 22 provides a flat interface attachment surface to which a variety of prostheses may be attached.

In the alternative embodiment of FIGS. 8–11, a coupling 50 provides the desired interfaces and retention of the prosthesis 52 on the pylon 54. The coupling 50 is constructed of graphite or some other appropriately strong material.

The pylon coupling 50 includes a split sleeve 56 which surrounds the upper end of the prosthesis 52 and the lower or distal end of the prosthetic pylon 54. Tab members 58 are provided at the split in sleeve 56, and the tab members are provided with two centrally-located openings 60, FIG. 11, adapted to accommodate bolt and nut combinations 62. The bolt and nut combinations 62 can be tightened to cause the pylon coupling 50 to grip and cause a frictional adhesion of the upper end of the prosthesis 52 and the lower or distal end of the prosthetic pylon 54.

The pylon coupling 50 further preferably includes gripping or bracing means 64, shown in the preferred embodiment as angular projections located on the internal surface of the coupling 50 in the interstices between the prosthetic foot 52 and the prosthetic pylon 54. Gripping means 64 are so sized and shaped as to provide additional surface contact and improve the aforementioned frictional adhesion between the coupling 50, the pylon 54, and the prosthetic foot 52.

The tab members 58 associated with the split in the coupling 50 are adjacent the front of the prosthetic pylon 54, but those skilled in the art will understand that the aforementioned split and the tab members 58 associated therewith may alternatively be oriented toward the side or rear of the prosthetic foot 52, and still be within the scope of the present invention.

In the alternative embodiment of FIGS. 12–15, the desired mating interface of the lower prosthesis 70 and the pylon 72 is provided by shaping the upper end of prosthesis 70 into a mating configuration. This is preferably accomplished by forming the desired curvature in the attachment portion of the prosthesis 70. When the prosthesis 70 is fabricated from certain deformable materials (such as aluminum or the like), however, the curvature may be provided during subsequent fabrication steps, such as by stamping the curvature into the prosthesis 70.

By limiting the downward extension of the attachment surface, such as indicated at 74, the attachment surface will cause a minimum of interference with the flexural performance of the prosthesis 70.

Although a nut, bolt and barrel washer combination 76 is illustrated in FIGS. 12–14 for attaching the components of this embodiment, many alternative attachment means may be utilized, such as the hose clamp 78 illustrated in FIG. 15.

The embodiment of FIGS. 16–18 is similar to that of FIGS. 12–14, but illustrates an alternative method of forming the curvilinear attachment interface 80 on the upper end of the prosthesis 82. In this embodiment, the interface 80 is preferably formed during manufacture or fabrication of the prosthesis 82, and is shaped to matingly engage the exterior of the pylon 84. Alternative methods of manufacture would include depositing material (such as graphite or the like) on the prosthesis 82 after the prosthesis has been manufactured.

Similar to the embodiment of FIGS. 12–15, the components of FIGS. 16–18 may be operatively retained in their desired assembled form by any expedient means, such as, for example, nut, bolt and barrel washer combinations and/or hose clamps.

Figure 21:
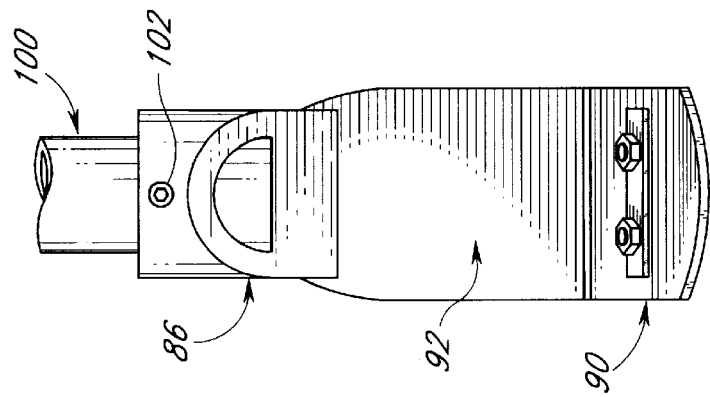
FIG. 21 is a front elevation view, taken along line 21—21 of FIG. 20.
Figure 20:
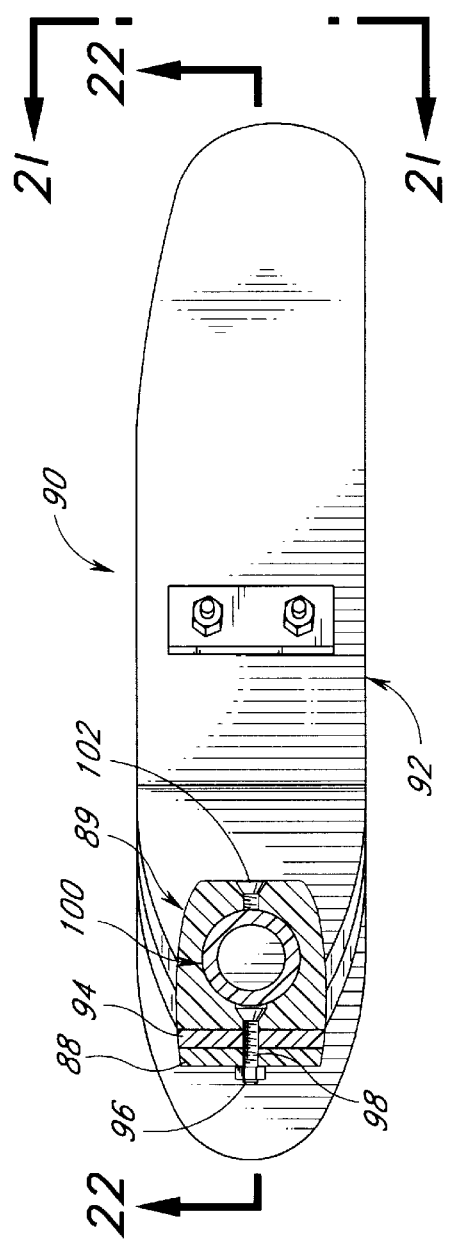
FIG. 20 is a partially sectional plan view, taken along line 20—20 of FIG. 19.

The embodiment of FIGS. 19–22 is similar to that of FIGS. 8–11, but illustrates an alternative construction of a bracket member 86 and its corresponding preferred assembly with a prosthesis. The coupling bracket 86 is operatively attached to an upper end 88 of a foot prosthesis 90, through the use of attachment means. An auxiliary ankle member 92 may be utilized with the foot, with an upper portion 94 interposed between the bracket 86 and the foot 90.

The attachment of the bracket 86 to the foot portion 88 and/or auxiliary ankle portion 94 is preferably demountable, such as by the provision of nut and bolt assemblies 96 disposed through corresponding holes 98, to permit ready interchangeability of components of the prosthesis. Alternative embodiments would, of course, include permanently bonding the bracket 86 to the foot and/or auxiliary ankle member.

The pylon 100 may preferably be positioned at any of a range of heights within the bracket 86, by the provision of retaining means such as a set screw 102 or the like. By tightening the screw 102, the pylon may be frictionally retained in a desired position with respect to the bracket 86. Permanent retention means may be utilized to permanently bond, for example, the pylon 100 into the bracket 86.

To reduce the weight of the assembly, the front of the bracket 86 may include a sloping face, as best shown in FIGS. 19 and 22. A limit-stop or safety ledge 104, FIG. 22, may be provided as part of the bracket 86 to prevent the pylon 100 from sliding too far through the bracket 86.

By the prosthetic construction of my invention I provide a simple construction which permits the ready and economic use of a popular cylindrical tubular pylon with any of a broad range of other prosthetic devices. The construction permits ready interchangeability and manufacture of the pylon and the other prosthetic devices.

Moreover, the various components and portions of the present invention may be provided in a variety of sizes, thicknesses, and materials which may be interchangeable with correspondingly-shaped components to permit fine-tuning of the prosthesis to the needs of the wearer thereof. The pylon assembly of my invention may also be used in combination with numerous prior art prosthetic devices to improve the performance of such prior art devices.

The prosthetic construction of my invention has been described with some particularity but the specific designs and constructions disclosed are not to be taken as delimiting of the invention in that various obvious modifications will at once make themselves apparent to those of ordinary skill in the art, all of which will not depart from the essence of the invention and all such changes and modifications are intended to be encompassed within the appended claims.

I claim:

1. A prosthesis for attachment to the lower end of a round pylon, said prosthesis comprising:

a coupling member having on one side a curved concave mating surface conforming substantially to a curved convex outer mating surface of said pylon and on an opposite side a substantially flat mating surface;

a foot member having an upper attachment section having on one side a substantially flat mating surface substantially conforming to said flat mating surface of said coupling member; and said mating surfaces being oriented substantially parallel to the longitudinal axis of said pylon when said corresponding conforming mating surfaces are mated together such that an axial load placed on said pylon produces a corresponding shear force on said mating surfaces in a direction substantially parallel to the longitudinal axis of said pylon.

2. The prosthesis of claim 1 further comprising an adhesive or bonding agent adapted to be disposed between said curved mating surfaces to maintain said pylon and said coupling member in substantially fixed operative relation.

3. The prosthesis of claim 1 further including a mounting member for selectively attaching and detaching said foot member to said lower end of said round pylon.

4. The prosthesis of claim 3 wherein said mounting member comprises a nut and bolt combination configured and arranged so as to provide a compressive force between said corresponding conforming mating surfaces such that said foot member and said pylon may be maintained in operative relation by frictional engagement of said mating surfaces.

5. The prosthesis of claim 4 wherein said nut and bolt combination extend through aligned holes formed in said coupling member and said upper attachment section of said foot member for providing said compressive force.

* * * * *